United States Patent
Murakami et al.

(10) Patent No.: US 8,342,046 B2
(45) Date of Patent: Jan. 1, 2013

(54) ENVIRONMENTAL TEST APPARATUS

(75) Inventors: Seiichi Murakami, Osaka (JP);
Katsuhiko Watabe, Osaka (JP);
Masayuki Yamauchi, Nagano (JP)

(73) Assignees: ESPEC Corp., Osaka (JP); Tiyoda Electric Co., Ltd., Nagano (JP)

( * ) Notice: Subject to any disclaimer, the term of this patent is extended or adjusted under 35 U.S.C. 154(b) by 423 days.

(21) Appl. No.: 12/363,186

(22) Filed: Jan. 30, 2009

(65) Prior Publication Data

US 2009/0133514 A1 May 28, 2009

Related U.S. Application Data

(62) Division of application No. 11/955,158, filed on Dec. 12, 2007, now Pat. No. 7,497,136.

(30) Foreign Application Priority Data

Dec. 13, 2006 (JP) ................................. 2006-335611
Dec. 13, 2006 (JP) ................................. 2006-335612

(51) Int. Cl.
*F28D 15/00* (2006.01)

(52) U.S. Cl. ..................................................... 73/865.6
(58) Field of Classification Search ........................ None
See application file for complete search history.

(56) References Cited

U.S. PATENT DOCUMENTS

| | | | | |
|---|---|---|---|---|
| 3,825,723 A | * | 7/1974 | Roeser | 219/401 |
| 3,886,791 A | * | 6/1975 | Grossman | 73/150 R |
| 4,572,427 A | * | 2/1986 | Selfridge et al. | 236/3 |
| 7,257,990 B2 | * | 8/2007 | Bujas et al. | 73/38 |
| 2006/0208098 A1 | * | 9/2006 | Shdaimah et al. | 236/44 C |

* cited by examiner

*Primary Examiner* — Robert R Raevis
(74) *Attorney, Agent, or Firm* — Osha Liang LLP

(57) ABSTRACT

A second tank for accommodating a sample is disposed within a first tank. A heater for heating gas is provided inside the second tank. A heater controller controls the heater such that temperature of gas becomes a set temperature. A heat conducting member is disposed such that one end of the heat conducting member is positioned in the gas inside the first or second tank and the other end is positioned in the humidifying water contained in the humidifier. The heat conducting member is made of material having higher thermal conductivity than that of gas inside the first or second tank.

4 Claims, 2 Drawing Sheets

ENVIRONMENTAL TEST APPARATUS

CROSS-REFERENCE TO RELATED APPLICATIONS

This application is a divisional application of the parent application, U.S. patent application Ser. No. 11/955,158, filed on Dec. 12, 2007.

BACKGROUND OF THE INVENTION

1. Field of the Invention

The present invention relates to an environmental test apparatus including a tank which accommodates a sample under a state where a constant temperature of inside gas is maintained.

2. Description of Related Art

JP-A-2005-121256 discloses an apparatus which executes tests including a test for checking operation condition of an electronic component under an environment where temperature and other conditions have been set at predetermined values. The apparatus shown in JP-A-2005-121256 includes a tank for accommodating a sample. The tank has a heating unit such as a heater, and the temperature of gas inside the tank is set at a predetermined value by appropriate control of the heating unit.

According to this type of apparatus, the gas temperature becomes excessively high when the gas in the tank is excessively heated. In this case, it may be difficult to maintain the gas temperature at the predetermined set value. For example, when an operation test is carried out for a sample which is an electronic component, heat is released from the electronic component. When a sample which generates heat is tested as in this case, positive cooling of the interior of the tank may be required.

When the tank is cooled from the outside of the tank, for example, gas existing around the inner surface of the tank is initially cooled. When the gas temperature reaches the dew point, moistures in the gas condense and adhere to the inner surface of the tank. In this case, the heat robbed from the gas by cooling is supplemented by condensation. Thus, the effect of cooling is difficult to reach the inside of the tank in some cases. Particularly when the tank has a multi-layer structure as in the structure disclosed in JP-A-2005-121256, only limited circulation of the gas occurs, and therefore the entire gas is further difficult to be cooled. When cooling the gas in the tank is difficult, excessive temperature increase of the gas inside the tank cannot be reduced. In this case, such a condition is possible where the temperature of the gas cannot be appropriately maintained at the set value.

SUMMARY OF THE INVENTION

It is an object of the invention to provide an environmental test apparatus capable of easily maintaining the temperature of gas inside a tank which has a multi-layer structure for accommodating a sample.

An environmental test apparatus provided according to an aspect of the invention includes: a first tank (as a first tank unit) which selectively switches between state where inside gas is sealed and state where the inside gas is opened to the outside; a second tank (as a second tank unit or passage unit) disposed within the first tank to accommodate a sample; a heater which heats gas inside the second tank; a heater controller which controls the heater such that the temperature of the gas inside the second tank becomes a set temperature; a humidifier which contains humidifying water and heats and evaporates the humidifying water to humidify the gas inside the second tank; a humidifier controller which controls the humidifier to heat the humidifying water to a temperature lower than the set temperature such that the humidity of the gas inside the second tank becomes a set humidity; and a heat conducting member made of material having higher thermal conductivity than that of gas inside the first or second tank, the heat conducting member being disposed such that one end of the heat conducting member is positioned in the gas inside the first or second tank and the other end is positioned in the humidifying water contained in the humidifier.

According to this aspect of the invention, heat shifts from the gas inside the first or second tank toward the humidifying water through the heat conducting member made of material having thermal conductivity higher than that of the gas. Thus, the gas inside the first and second tanks can be efficiently cooled.

BRIEF DESCRIPTION OF THE DRAWINGS

Other and further objects, features and advantages of the invention will appear more fully from the following description taken in connection with the accompanying drawings in which.

DESCRIPTION OF THE PREFERRED EMBODIMENT

Figure 1:
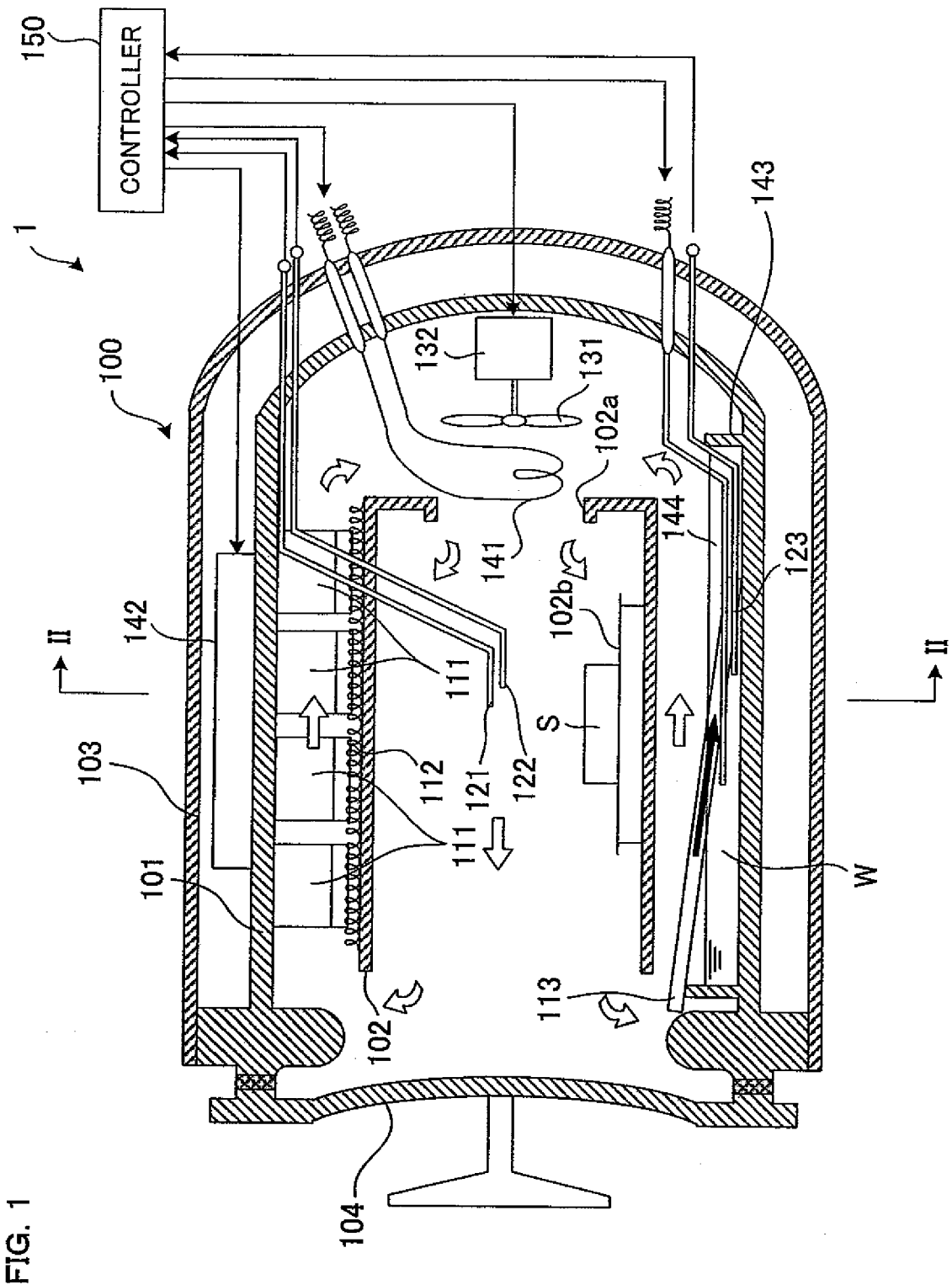
FIG. 1 illustrates an inside structure including a part of a cross section of an environmental test apparatus according to an embodiment of the invention.

FIG. 1 is a cross-sectional view of an environmental test apparatus 1 according to a preferred embodiment of the invention. The environmental test apparatus 1 has a test chamber 100 and a controller 150. The controller 150 controls the test environment such as the temperature of gas inside the test chamber 100. The controller 150 functions as either of a heater controller or humidifier controller of this invention.

The test chamber 100 has a multi-layer structure which combines an outer tank 103, a first inner tank 101, and a second inner tank 102 such that one tank fits inside another tank. These tanks are disposed in the order of the outer tank 103, the first inner tank 101, and the second inner tank 102 from the outside to the inside of the test chamber 100. The first and second inner tank 101 function as a first and second tank of this invention, respectively. The first inner tank 101 is accommodated in the outer tank 103, and the second inner tank 102 is accommodated in the first inner tank 101. A space is produced between the outer tank 103 and the first inner tank 101, and a cooling unit 142 is equipped in this space.

The first inner tank 101 is open to the left in FIG. 1. A cover 104 is provided on this opening. The cover 104 is supported by the first inner tank 101 via a not-shown opening and closing mechanism such that the close condition and the open condition can be selected. FIG. 1 shows the condition of the closed cover 104, in which state the interior of the first inner tank 101 is sealed. The opening and closing mechanism is constructed such that the sealed condition inside the first inner tank 101 can be maintained even when the pressure of the gas inside the first inner tank 101 is changed from the atmospheric pressure, and designed such that the user of the test chamber 100 can manually open and close the cover 104. According to the environmental test in this embodiment, it is assumed that the inside of the test chamber 100 is maintained at a pressure extremely higher than the atmospheric pressure.

The second inner tank 102 is open to the left in FIG. 1. A through hole 102a penetrating through the second inner tank 102 in the left-right direction is formed at the right end of the second inner tank 102. A sample table 102b is provided within the second inner tank 102.

A heater 141 is equipped in a space between the first inner tank 101 and the second inner tank 102 on the right side of the through hole 102a in FIG. 1. A ventilation fan 131 is disposed on the right side of the heater 141. A rotation shaft of the ventilation fan 131 is fixed to a driving shaft of a driving motor 132. When the driving motor 132 is actuated, the fan 131 starts rotation and generates airflow toward the left. Thus, airflow in the direction indicated by white arrows in FIG. 1 is generated within the first inner tank 101 and the second inner tank 102. This airflow introduces gas heated by the heater 141 through the through hole 102a into the second inner tank 102, thereby circulating gas inside the first inner tank 101 and the second inner tank 102. Both the heater 141 and the driving motor 132 are connected with the controller 150. The controller 150 switches ON/OFF condition of the heater 141, and controls actuation of the driving motor 132.

A humidifier 143 is equipped at a lower position of the first inner tank 101. The humidifier 143 is fixed on the inner bottom surface of the first inner tank 101, and stores humidifying water W. The humidifier 143 has a heater 144, and a heating area of the heater 144 is soaked in the humidifying water W of the humidifier 143. When the heater 144 is actuated, the humidifying water W is heated. The changed temperature of the humidifying water W changes the humidity inside the test chamber 100. The heater 144 is connected with the controller 150. The controller 150 switches ON/OFF condition of the heater 144. The controller 150 thus adjusts the humidity of the gas inside the test chamber 100 to a predetermined value.

A dry-bulb temperature sensor 121 and a wet-bulb temperature sensor 122 are provided in the test chamber 100. Both the dry-bulb temperature sensor 121 and the wet-bulb temperature sensor 122 are disposed inside the second inner tank 102. The dry-bulb temperature sensor 121 and the wet-bulb temperature sensor 122 are connected with the controller 150, and signals indicating temperatures detected at detecting portion of these sensors 121 and 122 are transmitted to the controller 150. The controller 150 calculates the temperature and humidity of the gas inside the inner tank 102 based on the signals received from the dry-bulb temperature sensors 121 and the wet-bulb temperature sensor 122. A water temperature sensor 123 is also provided for the humidifying water W. The temperature detected by the water temperature sensor 123 is chiefly used for the control of the heater 144 for humidity adjustment.

By using the structure discussed above, the controller 150 calculates the temperature and humidity of the gas inside the second inner tank 102, and controls the heaters 141 and 144 and the driving motor 132 such that the temperature and humidity of the gas inside the second inner tank 102 become set temperature and set humidity established beforehand based on the calculated results. By this control, the gas inside the second inner tank 102 is maintained under predetermined environment corresponding to the set temperature and set humidity. Then, test for a sample S placed on the sample table 102b is carried out under the predetermined environment. For example, the temperature and humidity inside the second inner tank 102 are set at 130° C. and 85%, respectively. Then, in case of an electronic circuit given as the sample S, the operation of the electronic circuit as the sample S is tested under the condition of the set temperature and set humidity.

When the temperature of the gas inside the second inner tank 102 rapidly increases by the heat generated from the sample S or for other reasons, for example, temperature control only by the heater 141 and the driving motor 132 may be insufficient for the level of this temperature increase in the second inner tank 102. For avoiding this situation, the cooling unit 142 cools the first inner tank 101 under control of the controller 150 based on the signals from the dry-bulb temperature sensor 121 when predetermined conditions concerning the temperature of the gas inside the second inner tank 102 are satisfied.

When the cooling unit 142 starts cooling the first inner tank 101, the inside gas is initially cooled from the vicinity of the inner surface of the first inner tank 101. When the temperature of the gas in the vicinity of the inner surface of the first inner tank 101 reaches the dew point, condensation is produced on the inner surface of the first inner tank 101. When the set temperature and set humidity are 130° C. and 85%, for example, the dew point of the gas satisfying these set conditions becomes 124.6° C. In this case, the difference between the set temperature of 130° C. and the dew point is small, and thus the temperature easily reaches the dew point by cooling. When the condensation is produced on the inner surface of the first inner tank 101, most of the condensed dew flows downward along the inner surface of the first inner tank 101. In this case, a part of the dew flows into the humidifying water of the humidifier 143. Heat robbed from the gas inside the first inner tank 101 as a result of cooling by the cooling unit 142 is supplemented by heat generated through condensation thus produced. Thus, the gas inside the first inner tank 101 is not easily cooled, and the gas inside the second inner tank 102 provided further inside the first inner tank 101 is more difficult to be cooled.

Figure 2:
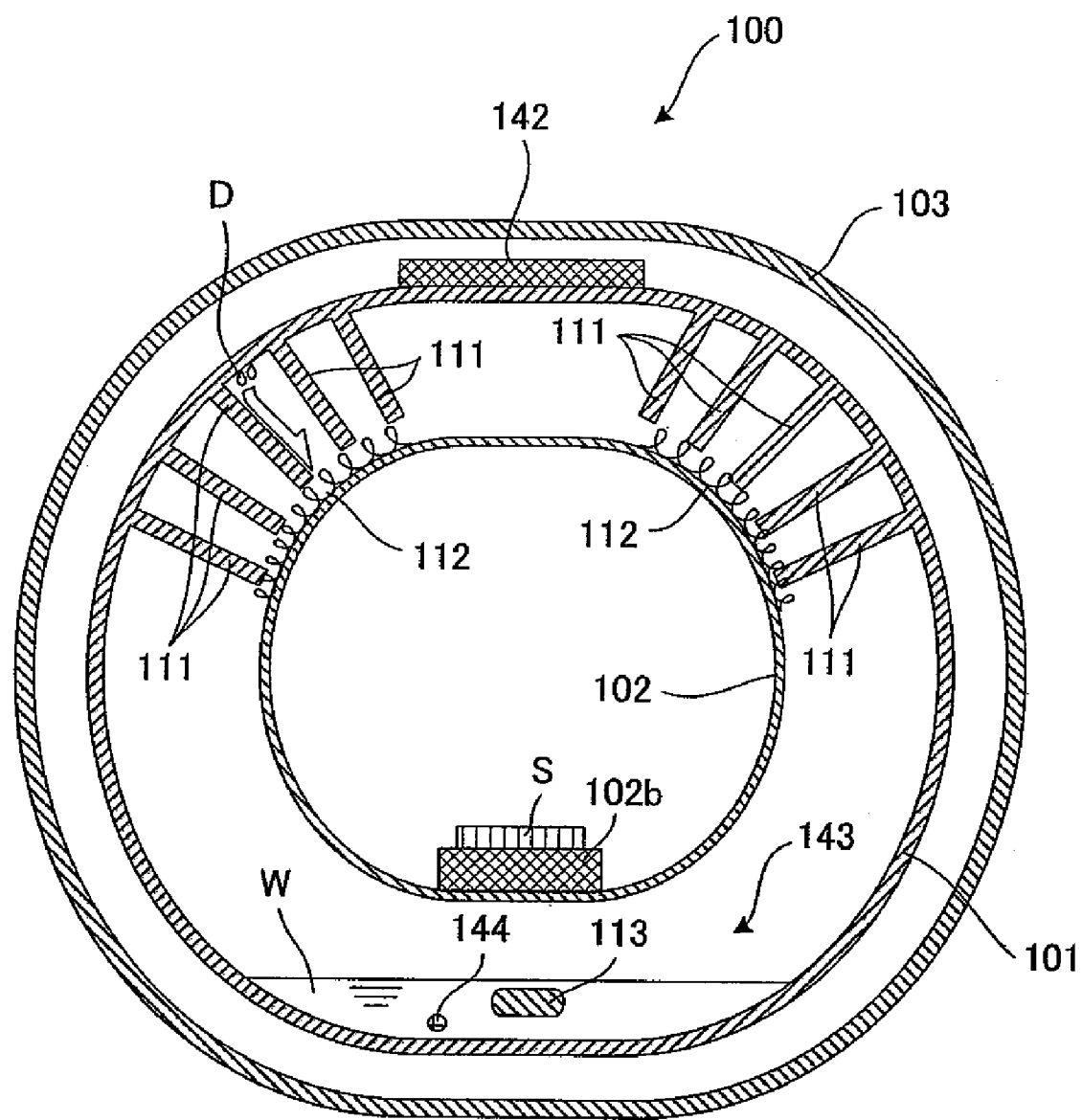
FIG. 2 is a cross-sectional view taken along a line II-II in FIG. 1.

For overcoming these drawbacks, the test chamber 100 according to this embodiment has protruding portions 111 protruding from the inner surface of the first inner tank 101. FIG. 2 is a cross-sectional view of the test chamber 100 taken along a line II-II in FIG. 1. As illustrated in FIG. 2, the first inner tank 101 has the plural protruding portions 111. Each upper end of the protruding portions 111 is fixed to the inner surface of the first inner tank 101, and each lower end is disposed in the vicinity of the outer surface of the second inner tank 102. Each of the protruding portions 111 has a flat plate shape. All the protruding portions 111 disposed on the left half of the first inner tank 101 extend from the inner surface of the first inner tank 101 toward the lower right in FIG. 2. All the protruding portions 111 disposed on the right half of the first inner tank 101 extend from the inner surface of the first inner tank 101 toward the lower left in FIG. 2.

Stainless steel wools 112 are fixed to the outer surface of the second inner tank 102. Stainless steel wools 112 functions a blocking portion of this invention. The stainless steel wools 112 are disposed between the lower ends of the protruding portions 111 and the second inner tank 102.

A heat pipe 113 is soaked in the humidifying water W stored in the humidifier 143. The heat pipe 113 is a bar-shaped component made of stainless steel or other material. One end of the heat pipe 113 is disposed above the left end of the humidifier 143 as illustrated in FIG. 1. The other end of the heat pipe 113 contacts the inner bottom surface of the humidifier 143. Thus, a part of the heat pipe 113 from one end to a predetermined length is exposed to above from the liquid level of the humidifying water W, and the remaining part is soaked below the liquid level.

Based on the structure discussed above, the second inner tank 102 is cooled in the following manner at the time of actuation of the cooling unit 142. When the first inner tank 101 is cooled, condensation is produced on the inner surface of the first inner tank 101. Condensed dew D generated by this condensation flows along the inner surface of the first inner tank 101 and the protruding portions 111 toward the outer surface of the second inner tank 102 in the direction indicated by a white arrow in FIG. 2. The condensed dew having reached the outer surface of the second inner tank 102 is retained by the stainless steel wools 112. The gas inside the second inner tank 102 has a high temperature higher than the set temperature due to heat generated from the sample S or for other reasons. When the set temperature and set humidity are 130° C. and 85%, for example, the temperature of the gas inside the second inner tank 102 is higher than 130° C. In this condition, the dew point is 124.6° C. Since the temperature of the second inner tank 102 is higher than the dew point, the condensed dew retained by the stainless steel wools 112 evaporates. At this time, heat of vaporization is robbed from the outer surface of the second inner tank 102 by the evaporation of the condensed dew. As a result, the second inner tank 102 is cooled, and the gas inside the second inner tank 102 is cooled accordingly.

When the set temperature and set humidity are 130° C. and 85%, for example, the water temperature of the humidifying water is set at 124.6° C. Since the temperature of the humidifying water W is set at the set temperature or lower, a large difference is produced between the temperature of the gas and the temperature of the humidifying water W when the temperature of the gas inside the second inner tank 102 increases to a temperature higher than the set temperature. Thus, heat moves from the gas to the humidifying water W through the heat pipe 113 in the direction indicated by a black arrow in FIG. 1. As a result, the gas inside the second inner tank 102 is cooled.

As apparent from above, the condensed dew produced on the inner surface of the first inner tank 101 is guided through the protruding portions 111 toward the second inner tank 102, and is evaporated on the outer surface of the second inner tank 102. Thus, even when condensation is produced on the inner surface of the first inner tank 101, the second inner tank 102 is cooled by evaporation of the condensed dew on the outer surface of the second inner tank 102. As a result, the gas inside the second inner tank 102 is cooled.

In addition, the stainless wools 112 hold the condensed dew having reached the outer surface of the second inner tank 102. In other words, the stainless steel wools 112 have a function of blocking the downward flow of the condensed dew along the outer surface of the second inner tank 102. Thus, the condensed dew is easily retained on the outer surface of the second inner tank 102, and easily evaporated on the outer surface of the second inner tank 102 before the condensed dew flows downward to a lower position of the second inner tank 102.

Moreover, since the heat of the gas inside the first inner tank 101 and the second inner tank 102 moves to the humidifying water W through the heat pipe 113, the gas is easily cooled. It is preferable that the heat pipe 113 is made of material having highest possible thermal conductivity. However, any material may be used as long as it has higher thermal conductivity than that of the gas inside the first inner tank 101 and second inner tank 102.

Modified Example

While the preferred embodiment according to the invention has been described herein, the invention may be practiced otherwise without departing from the scope of the invention. For example, the following modifications may be made.

While the stainless steel wools 112 are used in this embodiment, any part or structure may be used as long as it can block the downward flow of the condensed dew on the outer surface of the second inner tank 102. For example, a plurality of grooves extending in parallel with the horizontal direction may be formed on the outer surface of the second inner tank 102 to enlarge the surface area of the outer surface. When a component for retaining the condensed dew such as stainless steel wools 112 is used, it is preferable that the component is made of material having the highest possible thermal conductivity.

While the bar-shaped heat pipe 113 is used in this embodiment, a component having a shape different from the bar shape may be used. For example, a component having a shape different from the shape of the heat pipe 113 and adjusted such that one end of the component reaches the inside of the second inner tank 102 with the other end soaked in the humidifying water W may be used as a member having the same function as that of the heat pipe 113.

According to this embodiment, the test chamber 100 has both the protruding portions 11 and the heat pipe 113. However, the test chamber 100 need not have both the protruding portions 111 and the heat pipe 113 but may contain either one of these. Since the protruding portions 111 and the heat pipe 113 are components functioning independently from each other, the advantage that the gas inside the second inner tank 102 is easily cooled can be offered when only either the protruding portions 111 or the heat pipe 113 is equipped.

While the cooling unit 142 is contained in the test chamber 100 in this embodiment, the environmental test apparatus 1 need not include the cooling unit 142. In this case, the test chamber 100 is cooled by using a certain cooling unit from the outside of the outer tank 103 or a component (not shown) covering the outside of the outer tank 103 is removed from the outer tank 103 so as to promote heat release from the test chamber 100 at the time of excessive increase in the temperature of the gas inside the second inner tank 102.

While this invention has been described in conjunction with the specific embodiments outlined above, it is evident that many alternatives, modifications and variations will be apparent to those skilled in the art. Accordingly, the preferred embodiments of the invention as set forth above is intended to be illustrative, not limiting. Various changes may be made without departing from the spirit and scope of the invention as defined in the following claims.

What is claimed is:

1. An environmental test apparatus, comprising:
a tank unit which selectively switches between state where inside gas is sealed and state where the inside gas is opened to the outside;
a passage unit which, within the tank unit, defines an internal passage space for accommodating therein a test piece, the internal passage space being extended from an opening formed at one end to another opening formed at another end;
a heater which heats gas inside the passage unit;
a heater controller which controls the heater such that the temperature of the gas inside the passage unit becomes a set temperature;
a humidifier which contains humidifying water and heats and evaporates the humidifying water to humidify the gas inside the passage unit;
a humidifier controller which controls the humidifier to heat the humidifying water to a temperature lower than the set temperature such that the humidity of the gas inside the passage unit becomes a set humidity; and a heat conducting member made of material having higher thermal conductivity than that of gas inside the tank unit or the passage unit, the heat conducting member being disposed such that one end of the heat conducting member is positioned in the gas inside the tank unit and the other end is positioned in the humidifying water contained in the humidifier, wherein the heat conducting member and a water surface of the humidifying water intersect at a position apart from the other end relative to a direction along the water surface of the humidifying water.

2. The environmental test apparatus according to claim 1, wherein a part of the heat conducting member in the humidifying water is extended in an oblique angle with respect to the water surface.

3. The environmental test apparatus according to claim 1, wherein the passage unit has two openings, and a fan which generates an airflow that flows from a space between a wall of the tank unit and the passage unit into the passage unit via one of the openings and flows out from the passage unit via the other one of the openings; and wherein a portion of the heat conducting member outside the humidifying water is disposed in the path of the airflow generated by the fan.

4. An environmental test apparatus, comprising:

a tank unit which selectively switches between state where inside gas is sealed and state where the inside gas is opened to the outside;

a passage unit which, within the tank unit, defines an internal passage space for accommodating therein a test piece, the internal passage space being extended from an opening formed at one end to another opening formed at another end;

a heater which heats gas inside the passage unit;

a heater controller which controls the heater such that the temperature of the gas inside the passage unit becomes a set temperature;

a humidifier which contains humidifying water and heats and evaporates the humidifying water to humidify the gas inside the passage unit;

a humidifier controller which controls the humidifier to heat the humidifying water to a temperature lower than the set temperature such that the humidity of the gas inside the passage unit becomes a set humidity;

a heat conducting member made of material having higher thermal conductivity than that of gas inside the tank unit or the passage unit, the heat conducting member being disposed such that one end of the heat conducting member is positioned in the gas inside the tank unit and outside the humidifier and the other end is positioned in the humidifying water contained in the humidifier; and a fan configured, at the passage, to generate an airflow that flows from a space between a wall of the tank unit and the passage unit into the passage unit via the opening at the one end and flows out from the passage unit via the opening at the other end, wherein a portion of the heat conducting member outside the humidifier is disposed in the path of the airflow generated by the fan.

* * * * *